United States Patent
Chodorow et al.

(10) Patent No.: US 9,717,575 B2
(45) Date of Patent: Aug. 1, 2017

(54) HYBRID DENTAL TOOL WITH DETACHABLE PICKS

(71) Applicant: Sacks Holdings, Inc., Solana Beach, CA (US)

(72) Inventors: Devin S. Chodorow, Rancho Santa Fe, CA (US); Ingram S. Chodorow, Rancho Santa Fe, CA (US)

(73) Assignee: SACKS HOLDINGS, INC., Solana Beach, CA (US)

( * ) Notice: Subject to any disclaimer, the term of this patent is extended or adjusted under 35 U.S.C. 154(b) by 0 days.

(21) Appl. No.: 14/546,901

(22) Filed: Nov. 18, 2014

(65) Prior Publication Data

US 2016/0038263 A1    Feb. 11, 2016

Related U.S. Application Data

(60) Provisional application No. 62/036,028, filed on Aug. 11, 2014.

(51) Int. Cl.
| | | |
|---|---|---|
| *A61C 15/00* | (2006.01) | |
| *A61C 15/04* | (2006.01) | |
| *A61C 15/02* | (2006.01) | |

(52) U.S. Cl.
CPC ............ *A61C 15/046* (2013.01); *A61C 15/02* (2013.01)

(58) Field of Classification Search
CPC ......... A61C 15/00; A61C 15/02; A61C 15/04; A61C 15/046; A46B 15/0071; A46B 15/0055; A45D 44/18
See application file for complete search history.

(56) References Cited

U.S. PATENT DOCUMENTS

| | | | | |
|---|---|---|---|---|
| 869,175 A | * | 10/1907 | Gorut | A61C 15/02 132/328 |
| 958,335 A | * | 5/1910 | Strock | A61C 15/02 132/328 |
| 1,417,518 A | | 5/1922 | Henerlau | |
| 1,882,204 A | | 10/1932 | Zrna et al. | |
| 2,510,194 A | * | 6/1950 | Thomas | A61C 15/02 132/325 |
| 2,544,276 A | * | 3/1951 | Ness | A61C 7/00 132/326 |
| 3,783,883 A | * | 1/1974 | Alexander | A61C 15/046 132/323 |
| 5,113,880 A | | 5/1992 | Honda et al. | |
| 5,538,023 A | | 7/1996 | Oczkowski et al. | |
| 5,692,531 A | | 12/1997 | Chodorow et al. | |
| 5,829,458 A | | 11/1998 | Chodorow | |
| 5,931,171 A | | 8/1999 | Landis et al. | |
| 5,975,296 A | | 11/1999 | Dolan et al. | |
| D424,748 S | | 5/2000 | Dolan | |

(Continued)

*Primary Examiner* — Robyn Doan
(74) *Attorney, Agent, or Firm* — Kilpatrick Townsend & Stockton LLP

(57) ABSTRACT

A hybrid dental tool is disclosed herein. The hybrid dental tool includes a flosser having a flossing head. The flossing head can include a filament stretching between the first arm and a second arm. The flossing head can include a pick receptacle. The hybrid dental tool can further include a pick that has a first end and a second end. The pick can be sized and shaped to fit within the pick receptacle such that the first and second ends are protected. The pick can releasably connect with the flossing head to allow the separation of the pick from the flossing head.

19 Claims, 8 Drawing Sheets

(56) References Cited

U.S. PATENT DOCUMENTS

| | | | |
|---|---|---|---|
| 6,065,479 A | 5/2000 | Chodorow et al. | |
| 6,085,760 A | 7/2000 | Chodorow et al. | |
| 6,752,158 B1 | 6/2004 | Gwen | |
| D493,575 S * | 7/2004 | Gwen | D28/65 |
| 7,234,475 B2 | 6/2007 | Ding et al. | |
| D578,254 S | 10/2008 | Grendol | |
| 7,487,785 B2 | 2/2009 | Dougan et al. | |
| D637,762 S | 5/2011 | Nanda | |
| 8,079,374 B2 | 12/2011 | Chodorow et al. | |
| 8,375,961 B2 | 2/2013 | Prokopchuk et al. | |
| D681,879 S | 5/2013 | Fisher et al. | |
| 8,522,798 B2 | 9/2013 | Kollar et al. | |
| D750,326 S | 2/2016 | Lannie | |
| D765,915 S | 9/2016 | Lannie et al. | |
| D777,377 S | 1/2017 | Dudley et al. | |
| 9,554,663 B2 | 1/2017 | Truog et al. | |
| 2002/0020427 A1* | 2/2002 | Lin | A61C 15/046 132/325 |
| 2005/0048439 A1* | 3/2005 | Gwen | A61C 15/02 433/141 |
| 2011/0132392 A1* | 6/2011 | Crisp | A46B 15/0055 132/309 |
| 2012/0111348 A1* | 5/2012 | Prokopchuk | A61C 15/046 132/200 |
| 2014/0326274 A1* | 11/2014 | Kollar | A61C 15/046 132/323 |
| 2016/0113744 A1 | 4/2016 | Chodorow | |

\* cited by examiner

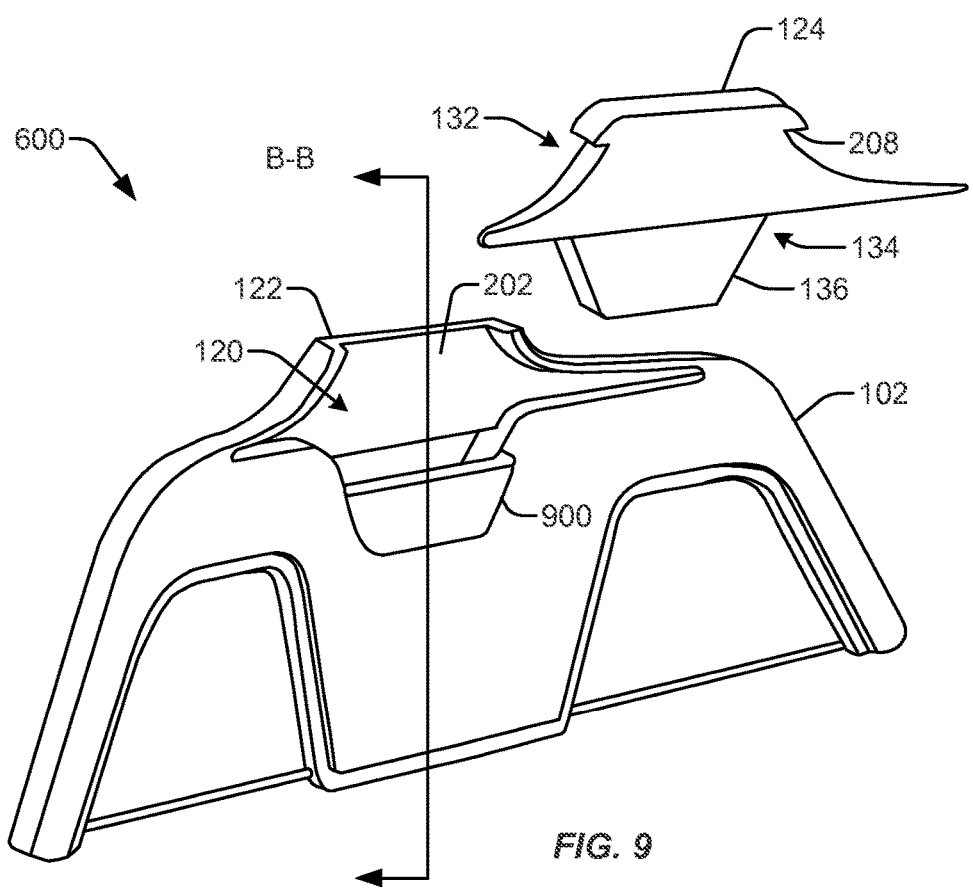
FIG. 9
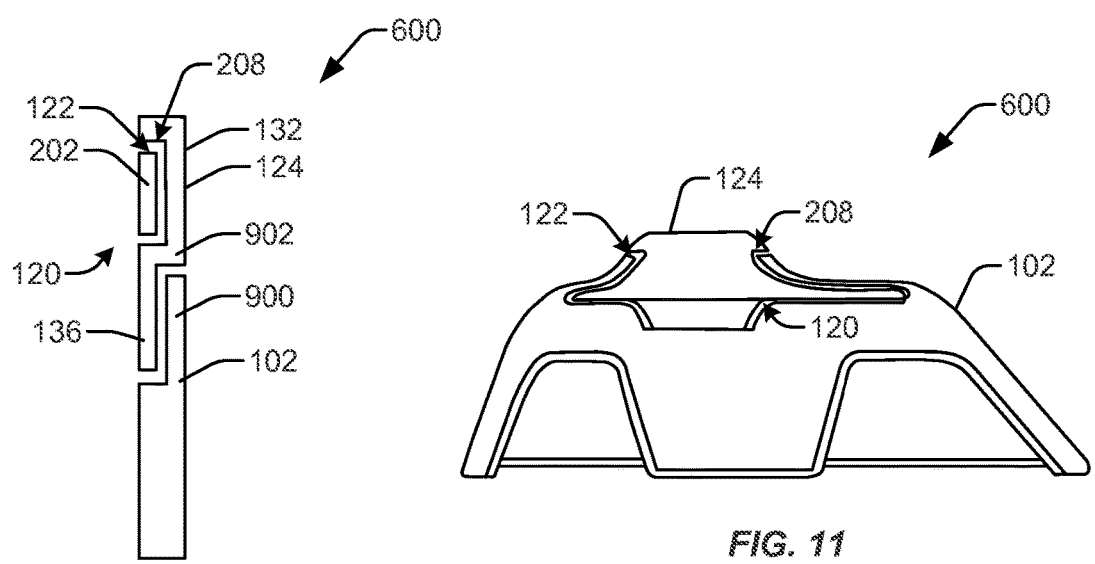
FIG. 10
FIG. 11

HYBRID DENTAL TOOL WITH DETACHABLE PICKS

CROSS-REFERENCES TO RELATED APPLICATIONS

This application claims the benefit of U.S. Provisional Application No. 62/036,028 entitled "HYBRID DENTAL TOOL WITH DETACHABLE PICKS," and filed on Aug. 11, 2014, the entirety of which is hereby incorporated by reference herein.

BACKGROUND

The present disclosure relates, generally, to dental devices, and more particularly to dental hygiene devices.

While dental hygiene has long been important in American and other cultures for maintaining a desirable physical appearance, recent discoveries have increased the urgency with which dental hygiene is maintained. These recent discoveries have linked oral bacteria to other, more serious disease such as, for example, heart disease. In light of the increased importance of dental hygiene, new devices are desired to improve dental hygiene.

BRIEF SUMMARY

One aspect of the present disclosure relates to a hybrid dental device. The hybrid dental device includes a pick having a first end and a second end and a longitudinal axis extending therebetween, and a flosser. The flosser can include a flossing head having a first arm extending in a first direction, a second arm extending in the first direction, and a filament extending from the first arm to the second arm. The hybrid dental device can include a pick receptacle that can receive the pick, which pick receptacle can protect the first and second ends of the pick when the pick is received within the pick receptacle.

In some embodiments, the pick receptacle is located on the flossing head. In some embodiments, the flossing head includes a third arm extending from the flossing head and a second filament extending from the third arm to the second arm. In some embodiments, the third arm extends in the first direction from the flossing head.

In some embodiments, the pick receptacle includes a capture feature configured to releasably capture the pick. In some embodiments, the pick includes a mating feature configured to mate with the capture feature of the flosser. In some embodiments, the capture feature and the mating feature can repeatedly capture the pick. In some embodiments, the capture feature includes at least one of: a pair of tabs, a receiving volume, a bracket, and an insert.

In some embodiments, the capture feature can include a bottom, a first wall extending in a second direction from the bottom, a second wall extending in a second direction from the bottom, which bottom and the first and second walls define a receiving channel, and which receiving channel can have a midline plane positioned between the first and second walls, a first tab extending from the first wall towards the midline plane, and a second tab extending from the second wall towards the midline plane. In some embodiments, the first tab and the second tab are non-coplanar. In some embodiments, the mating feature can be a third tab that can engage with both the first and second tabs. In some embodiments, this third tab can engage opposite sides of the first and second tabs. In some embodiments, this engagement can be a deformable engagement in that one or more of the first, second, and third tabs deform when the third tab is engaged with the first and second tabs so as to retain the pick in the pick receptacle.

In some embodiments, the pick and the flossing head can be different materials. In some embodiments, the flossing head can be a polymer having a first material property and the pick can be a polymer having a second material property, which second material property is different than the first material property. In some embodiments, the flosser can include a handle extending from the flossing head. In some embodiments, the pick receptacle can be located in the handle. In some embodiments, both the first and second ends of the pick are sized and shaped to allow insertion into the interproximal space between human teeth.

One aspect of the present disclosure relates to a hybrid dental device. The hybrid dental device can include a pick having a first end and a second end and a longitudinal axis extending therebetween, and a flosser including: a flossing head having a first arm extending in a first direction, a second arm extending in the first direction, and a filament extending from the first arm to the second arm. In some embodiments, the flosser can include a pick receptacle located on the flossing head, which pick receptacle can be sized and/or shaped to receive the pick. In some embodiments, the pick receptacle can be sized and/or shaped such that the first and second ends of the pick are protected when the pick is received within the pick receptacle.

In some embodiments, the pick receptacle can include a capture feature that can releasably capture the pick. In some embodiments, the pick can include a mating feature that can mate with the capture feature of the flosser. In some embodiments, the capture feature can include a bottom, a first wall extending in a second direction from the bottom, a second wall extending in a second direction from the bottom, which bottom and the first and second walls define a receiving channel, and which receiving channel includes a midline plane positioned between the first and second walls. In some embodiments, the capture feature can include a first tab extending from the first wall towards the midline plane, and a second tab extending from the second wall towards the midline plane. In some embodiments, the first tab and the second tab are non-coplanar, and the mating feature can be a third tab that can deformably engage with both the first and second tabs.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 9 is a perspective view of an embodiment of a hybrid dental tool that retains a pick with a front wall and a back wall.

FIG. 10 is a section view of the embodiment of the hybrid dental tool of FIG. 9.

FIG. 11 is a front view of the embodiment of the hybrid dental tool of FIG. 9.

In the appended figures, similar components and/or features may have the same reference label. Where the reference label is used in the specification, the description is applicable to any one of the similar components having the same reference label.

DETAILED DESCRIPTION OF THE INVENTION

In some embodiments, the present disclosure relates to a hybrid dental device and/or hybrid dental tool. In some embodiments, the hybrid dental tool can integrate multiple care devices into a single device. In some embodiments, the hybrid dental tool can include a flosser and one or several picks. In some embodiments, the one or several picks can be integrated into the flosser, and/or retained by the flosser. In one embodiment, the one or several picks can include a first end and a second end. In some embodiments, one or both of the first and second ends of the pick can be a dental hygiene tool, such as a tooth pick, that can, in some embodiments, be sized and shaped to allow insertion into the interproximal space between human teeth. In one particular embodiment, the one or several picks can be received in a pick receptacle. In some embodiments, the pick receptacle can be sized and shaped such that when the one or several picks are in the pick receptacle, the first and second ends of the pick are protected in that they are contained within the pick receptacle so as to be snag free.

For the purposes of explanation, the ensuing details are set forth in order to provide a thorough understanding of various embodiments. It will be apparent, however, to one skilled in the art that various embodiments may be practiced without some of these specific details. For example, various features may be shown as components of some specific embodiments. In other instances, previously known features may be shown without unnecessary detail in order to avoid obscuring the inventive features of the described embodiments.

Embodiments provided herein are examples only, and are not intended to limit the scope, applicability, or configuration of the disclosure. Rather, the ensuing description of the embodiments will provide those skilled in the art with an enabling description for implementing one or more embodiments. It should be understood that various changes may be made in the function and arrangement of elements without departing from the spirit and scope of the disclosed embodiments.

Figure 1:
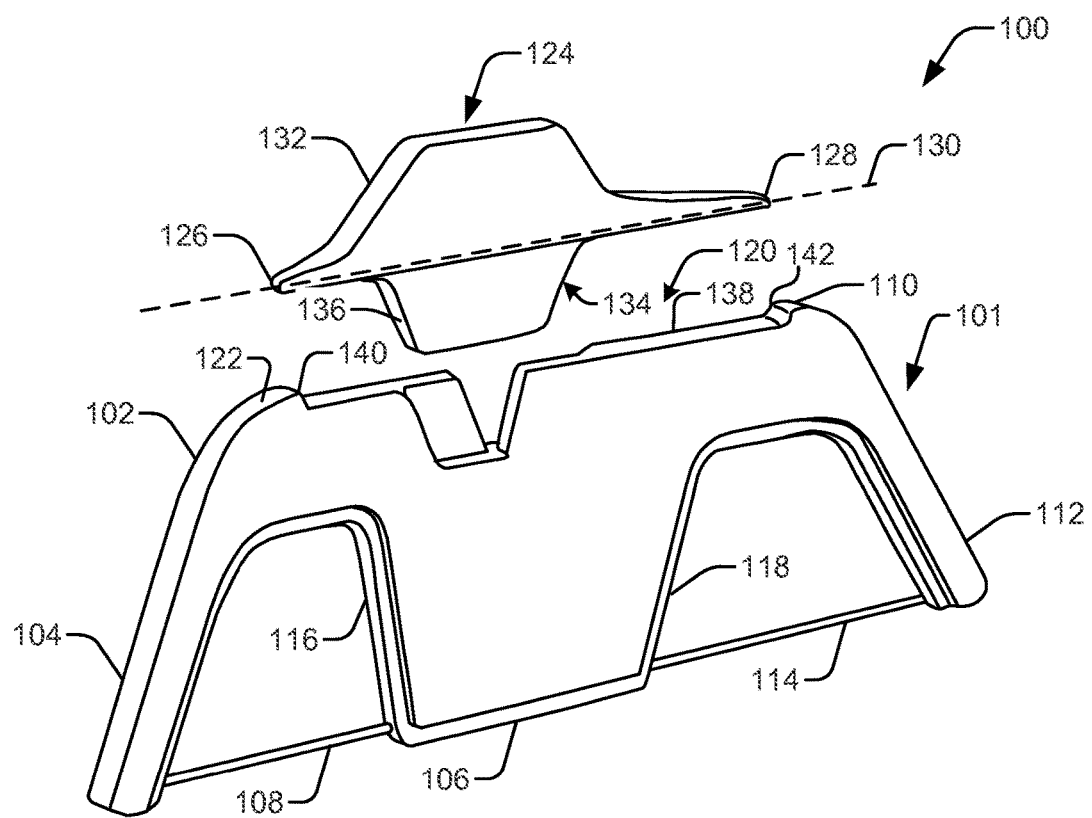
FIG. 1 is a perspective view of one embodiment of a disassembled hybrid dental tool.

With reference now to FIG. 1, a perspective view of one embodiment of hybrid dental tool 100 is shown. The hybrid dental tool 100 can comprise a variety of shapes and sizes. In some embodiments, the hybrid dental tool 100 can be sized so as to be easily held in a hand and to be used within a mouth. The hybrid dental tool 100 can be made from a variety materials. In some embodiments, the hybrid dental tool 100 can be made from one or several plastics, metals, composites, polymers, or the like. In some embodiments, the materials for the hybrid dental tool 100 are selected based on desired properties of a hybrid dental tool and/or of the specific portion of the hybrid dental tool.

The hybrid dental tool 100 can include a flosser 101. The flosser 101 can include a flossing head 102, also referred to herein as a flossing portion. The flossing head 102 can include features configured to allow use of the hybrid dental tool 100 in flossing the teeth. The flossing head 102 can comprise a variety of shapes and sizes, and in some embodiments, can be sized and shaped so as to allow a user to access all of the teeth in the user's mouth, and particularly the teeth located in the rear of the mouth.

The flossing head 102 can include a first arm 104, also referred to herein as a leading arm, and a second arm 106, also referred to herein as a trailing arm. In some embodiments, the first arm 104 can be located at the front of the flossing head 102 and/or of the flosser 101 and the trailing arm 106 can be relatively more centrally located in the flosser 101. In some embodiments, the leading arm 104 and the trailing arm 106 are parallel, and in some embodiments, the leading arm 104 and the trailing arm 106 are nonparallel. In some embodiments, the first and second arms 104, 106 can extend in the same direction. In some embodiments, the first and second arms 104, 106 extend in the same direction if they are parallel, and in some embodiments, the first and second arms 104, 106 extend in the same direction if a component of the extension of the first and second arms 104, 106 is parallel.

In some embodiments, the leading arm 104 and the trailing arm 106 both extend from a link arm 110 and can be connected by a first filament 108. This connection of the leading arm 104, the trailing arm 106, and the link arm 110 can create a U-shaped portion of the flossing head 102. In some embodiments, the connection of the leading arm 104, the trailing arm 106, and link arm 110 can create other shapes such as, for example, a C-shape, a trapezoidal shape, or the like.

In some embodiments, the first filament 108 can be a thin single fiber and/or group of fibers that is/are sized, shaped, and configured for insertion between the patient's teeth into, for example, the interproximal space. This first filament 108 can comprise any lubricious fiber sufficiently strong and thin to be used for dental hygiene. In some embodiments, the first filament 108 can comprise any dental floss including, for example, a waxed fiber such as a nylon or cotton fiber, a polytetrafluoroethylene (PTFE) fiber, an ultra-high-molecular-weight polyethylene (UHMPE) fiber, or any other fiber. In some embodiments, the first filament 108 can comprise dental floss.

In some embodiments, the flosser 101 can comprise a single flosser, and in some embodiments, the flosser 101 can comprise a multiple flosser. In the embodiment, depicted in FIG. 1, the flosser 101 is a double flosser, also referred to herein as a twin flosser. In such a double flosser configuration, the flosser 101 includes a third arm 112 and a second filament 114 that extends between the third arm 112 and the second arm 106. In some embodiments, the second arm 106 can include a first portion 116 to which the first filament 108 connects, and a second portion 118 to which the second filament 114 connects. In some embodiments, the first and second portions 116, 118 of the second arm 106 can extend in the same direction away from the link arm 110, and in some embodiments, the first and second portions 116, 118 of the second arm 106 can extend in different directions away from the link arm 110.

In some embodiments, the second filament 114 can be a thin single fiber and/or group of fibers that is/are sized, shaped, and configured for insertion between the patient's teeth into, for example, the interproximal space. This second filament 114 can comprise any lubricious fiber sufficiently strong and thin to be used for dental hygiene. In some embodiments, second filament 114 can comprise any dental floss including, for example, a waxed fiber such as a nylon or cotton fiber, a polytetrafluoroethylene (PTFE) fiber, or any other fiber. In some embodiments, the second filament 114 can comprise dental floss.

In some embodiments, the first filament 108 and the second filament 114 can comprise a single filament that extends from the first arm 104 to the third arm 112, and in some embodiments, the first filament 108 can be separate from the second filament 114. In some embodiments, one or both of the first and second filaments 108, 114 can comprise a plurality of filaments such as, for example, two, three, four, five and/or any other or intermediate number of filaments. In some embodiments, the filaments of the plurality of filaments can be made from the same material, and in some embodiments, the filaments of the plurality of filaments can be made from different materials.

In some embodiments in which one or both of the first and second filaments 108, 114 comprises a plurality of filaments, the filaments of the plurality of filaments can be positioned adjacent to each other such that the plurality of filaments can simultaneously clean a single interproximal space. In one specific embodiment, both the first and second filaments 108, 114 can comprise a plurality of filaments, the first filament 108 can comprise a plurality of filaments, the second filament 114 can comprise a plurality of filaments, or neither the first nor second filaments 108, 114 can comprise a plurality of filaments.

As seen in FIG. 1, the flosser 101 includes a pick receptacle 120 along the top 122 of the link arm 110 between the first arm 104 and the third arm 112. The pick receptacle 120 can be configured to receive and/or retain a pick 124. The pick 124 can comprise a variety of shapes and sizes, and can be made from a variety of materials. In some embodiments, the pick 124 can be made from the same material as the flosser 101, and in some embodiments, the pick 124 can be made from a different material than the flosser 101. In some embodiments, for example, the pick 124 can be made from the same material, including, for example, the same polymer, having the same material properties as the flosser 101, and in some embodiments, the pick 124 can be made from a different material, including, for example a different polymer having different material properties than the flosser 101.

The pick 124 can comprise a first end 126, a second end 128, and a longitudinal axis 130 extending therebetween. In some embodiments, one or both of the first and second ends 126, 128 of the pick 124 can comprise a tool, including a dental hygiene tool such as, for example, a tooth pick, tongue scraper/cleaner, a scalar, a pick, a brush, a mirror, or the like. In some embodiments, one or both of the first and second ends 126, 128 of the pick 124 can be configured for cleaning between a humans teeth, and in some embodiments, can be sized and shaped to allow insertion into the interproximal space between human teeth.

The pick 124 can include a grip portion 132. The grip portion 132 can comprise a variety of shapes, sizes, and features. In some embodiments, the grip portion 132 can be sized and shaped to facilitate the gripping and manipulation of the pick 124. In some embodiments, the grip portion 132 can be located at a midpoint of the pick 124 such that the distance between the grip portion 132 and both the first and second ends 126, 128 is the same, and in some embodiments, the grip portion 132 can be located at a position other than the midpoint of the pick 124 such that the distance between the grip portion and the first and second ends 126, 128 is unequal. In some embodiments, the grip portion 132 can be located at one or both of the first and second ends 126, 128 of the pick 124.

In some embodiments, the pick 124 can include one or several mating features 134. The one or several mating features 134 can be configured to matingly engage with one or several features of the flosser 101. In the embodiment of the pick 124 depicted in FIG. 1, the one or several mating features 134 comprise insert 136.

Returning again to the pick receptacle 120 of the flosser 101, in some embodiments, the pick receptacle 120 can be sized to receive the pick 124, and specifically can have one or several dimensions larger than one or several corresponding dimensions of the pick 124 so as to thereby allow portions of the pick 124 to be received within the pick receptacle 120. In some embodiments, the pick receptacle 120 can be a depression in the flosser head 102, and specifically in the link arm 110 of the flosser head 102, and in some embodiments, the pick receptacle 120 can be, for example, located in a handle of the flosser 101.

In some embodiments, the pick receptacle 120 can include an end receptacle 138 that is bounded by a first end receptacle wall 140 and a second end receptacle wall 142. In some embodiments, the end receptacle 138 can be sized and shaped to receive at least one or both of the first and second ends 126, 128 of the pick 124, and can be particularly sized and shaped such that when the first and second ends 126, 128 are received within the end receptacle 138, the first and second ends 126, 128 are protected in that they are not exposed to snags. In some embodiments, the protected state of the first and second ends 126, 128 includes the receiving of the first and second ends 126, 128 such that all or portions of the first and second ends 126, 128 do not extend outside of the volume of the end receptacle 138 and/or of the pick receptacle 120.

Figure 2:
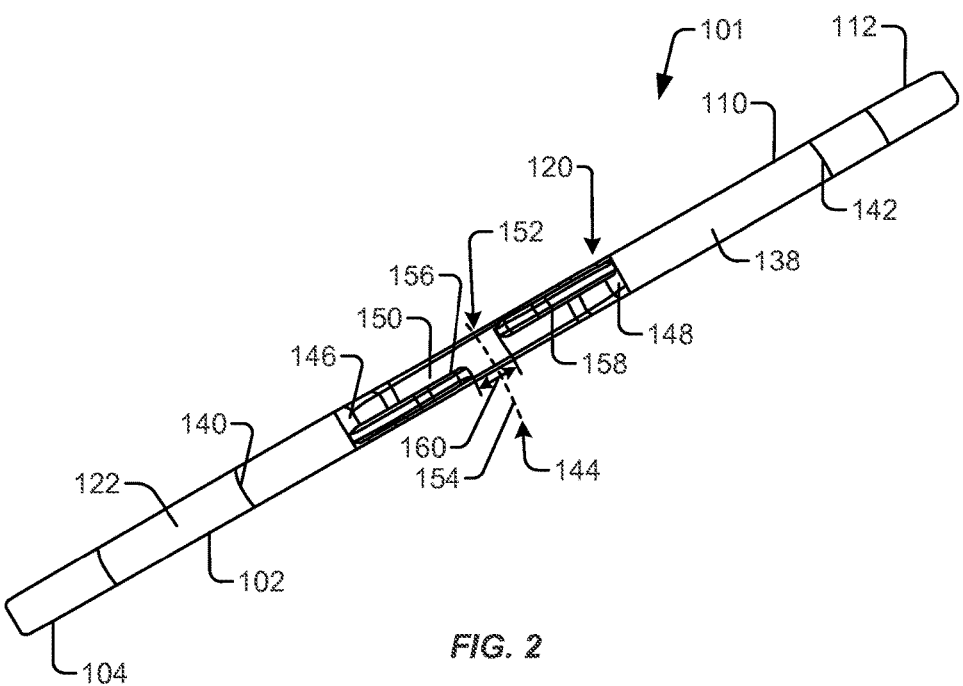
FIG. 2 is a top view of one embodiment of a flosser that is part of a hybrid dental tool.

With reference now to FIG. 2, a top view of one embodiment of flosser 101 is shown. The flosser 101 includes the flossing head 102 including the first arm 104 and the third arm 112 that are connected by the link arm 110. At the top 122 of the link arm 110 is the pick receptacle 120 that includes the end receptacle 138 defined by the first end receptacle wall 140 and the second end receptacle wall 142.

The pick receptacle 120 includes connection features 144, also referred to herein as connecting features 144 and/or capture features 144, that are configured to matingly engage with the mating features 134 of the pick 124 to releasably secure the pick 124 within the pick receptacle 120. In some embodiments, the mating engagement of the mating features 134 and the connecting features 144 can allow the repeatable securement of the pick 124 within the pick receptacle 120, and in some embodiments, the mating engagement of the mating features 134 and the connecting features 144 may not allow the repeatable securement of the pick 124 within the pick receptacle 120.

In the embodiment of FIG. 2, the connecting features comprise a first connection wall 146, also referred to herein as the first wall, a second connection wall 148, also referred to herein as the second wall, and a connection bottom 150 connecting the first and second walls 146, 148. In some embodiments, a plane can be located between, and defined by the first and second walls 146, 148. In the embodiment of FIG. 2, a midline plane 154 is located midway between the first and second walls 146, 148.

In the embodiment seen in FIG. 2, the first and second walls 146, 148 extend from proximate the top 122 of the flossing head 102 towards the first and second filaments 108, 114, and in connection with the connection bottom 150, create a connection receptacle 152. The connection receptacle 152 can comprise a variety of shapes and sizes. In some embodiments, the connection receptacle 152 can be sized to receive the mating features 134 of the pick 124, and specifically to receive the insert 136 of the pick 124.

In the embodiment of FIG. 2, a first tab 156 extends from the first wall 146 and towards the midline plane 154, and a second tab 158 extends from the second wall 148 and towards the midline place 154. In some embodiments, and additionally or alternatively, both the first and second tabs 156, 158 can extend from the connection bottom 150 towards the top 122 of the flossing head 102. These first and second tabs 156, 158 can be configured to matingly engage with the insert 136 of the pick 124 to releasably capture the pick 124 within the pick receptacle 120.

In some embodiments, the first tab 156 and the second tab 158 can extend in the same plane, and in some embodiments, and as depicted in FIG. 2, the first tab 156 and the second tab 158 can extend in different planes. In some embodiments, the first and second tabs 156, 158 can extend through a common plane that is parallel with the midline plane 144 or that is the midline plane 144. In the embodiment of FIG. 2, however, the first and second tabs 156, 158 do not extend through a common plane that is parallel with the midline plane 144 or that is the midline plane 144. Rather, in some embodiments, the first and second tabs 156, 158 can be separated by a space 160 that can be any desired shape and/or size. In some embodiments, this space 160 can facilitate the mating engagement of the first and second tabs 156, 158 with the insert 136.

Figure 2A:
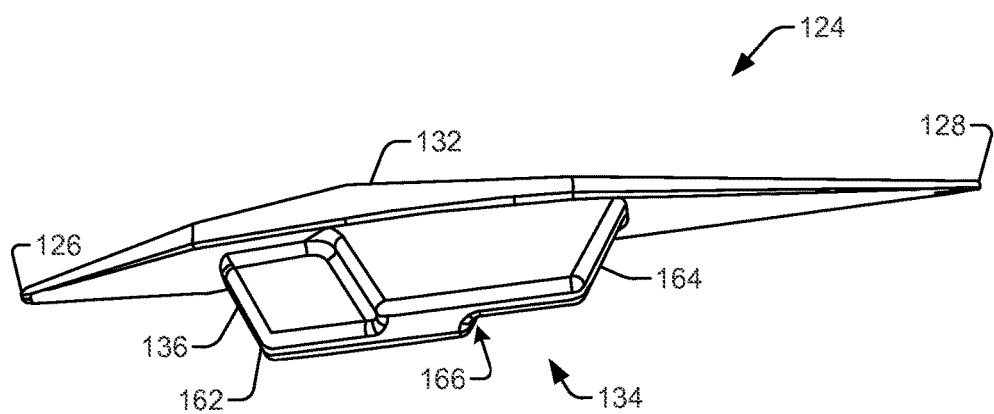
FIG. 2A is a perspective view of one embodiment of a pick that is a part of a hybrid dental tool.

With reference now to FIG. 2A, a perspective view of one embodiment of the pick 124 is shown. The pick 124 includes a first end 126, a second end 128, and a grip portion 132. The pick 124 additionally includes the mating feature 134, and specifically, the insert 136. The insert 136 is a stepped insert having a first planar portion 162 proximate to the first end 126, a second planar portion 164 proximate to the second end 128, and a step 166 connecting the first and second planar portions 162, 164. In some embodiments, the first and second planar portions 162, 164 can be sized, shaped, and/or positioned to engage with the first and second tabs 156, 158. Similarly, in some embodiments, the step 166 can be sized, shaped, and/or positioned to fit within the space 160.

Figure 3:
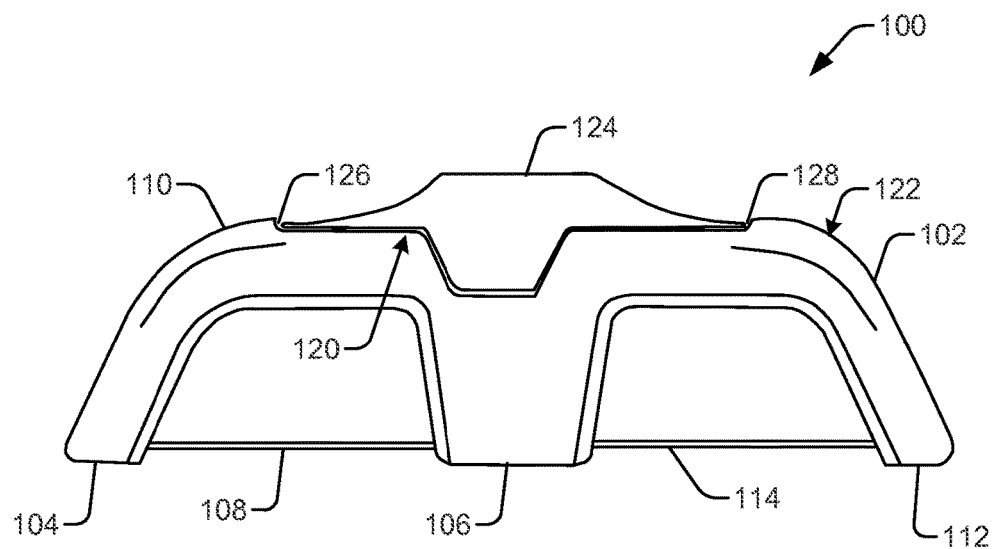
FIG. 3 is a front view of one embodiment of an assembled hybrid dental tool.

With reference now to FIG. 3, a front view of one embodiment of the hybrid dental tool 100 is shown. As seen, the hybrid dental tool 100 includes the flossing head 102 having the first arm 104 connected to the second arm 106 by the first filament 108 and the link arm 110, and the second arm 106 connected to the third arm 112 by the second filament 114 and the link arm 110. At the top 122 of the flossing head 102 is the pick receptacle 120. As seen in FIG. 3, the pick receptacle 120 receives portions of the pick 124, and specifically receives the first and second ends 126, 128 of the pick 124 such that the first and second ends 126, 128 are below the top 122 of the flossing head 102, and are thus within the volume of the pick receptacle 120.

Figure 4:
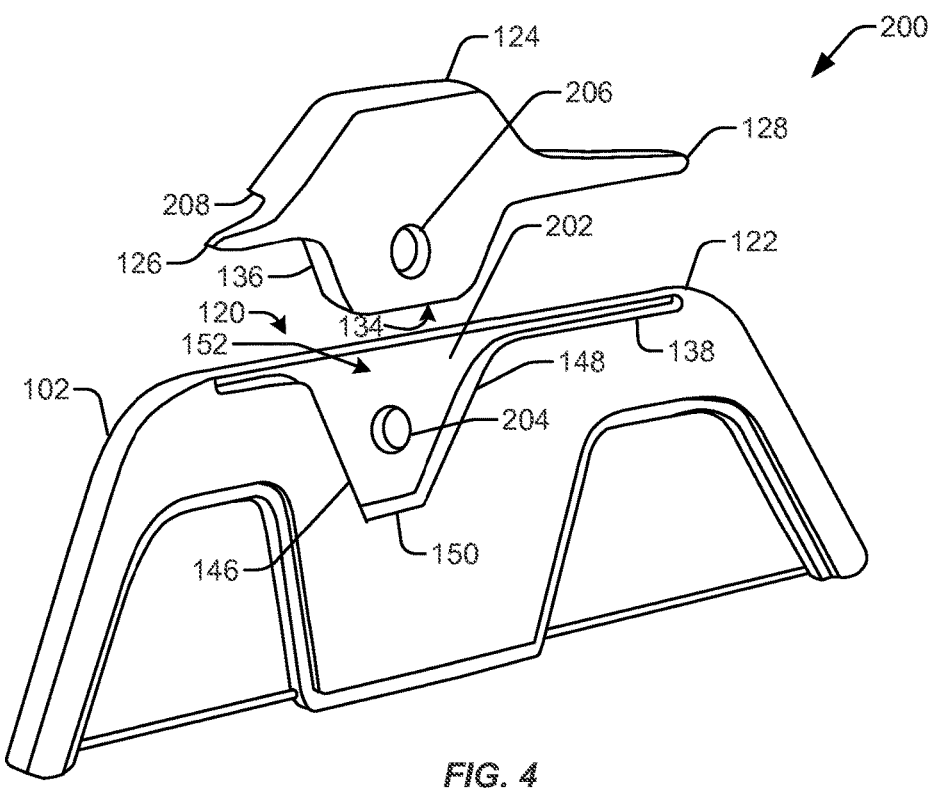
FIG. 4 is a perspective view of an embodiment of a hybrid dental tool that retains a pick with a retention insert.

With reference now to FIG. 4, a perspective view of an embodiment of a hybrid dental tool 200 is shown. This hybrid dental tool 200 includes the same features as the hybrid dental tool 100 with the exception of the pick receptacle 120, the connection features 144, and the mating features 134. The hybrid dental tool 200 includes the flossing head 102 having a top 122 and a pick receptacle 120. The pick receptacle 120 includes an end receptacle 138 that receives the first and second ends 126, 128 of the pick 124. The pick receptacle 120 additionally includes the first and second walls 146, 148, and the connection bottom 150, that together define the connection receptacle 152.

In contrast to the embodiment of FIG. 1, the hybrid dental tool 200 includes a back wall 202 that defines a boundary of the connection receptacle 152 that is perpendicular to one or both of the midline plane (not shown in FIG. 4) and the top 122. The back wall 202 can, in some embodiments, include a retention insert 204 that can be received by a mating receptacle 206 of the pick 124 to retain the pick 124 in the pick receptacle 120. The retention insert 204, and the mating receptacle 206, can comprise a variety of shapes and sizes. In one embodiment, the retention insert 204 can comprise a cylindrical protrusion, and the mating receptacle 206 can comprise a hole in the insert 136 of the pick 124.

As further seen in FIG. 4, the pick 124 includes an abutment face 208 that can be configured to abut with the top 122 of the back wall 202. In some embodiments, this abutment face 208 can stabilize the pick 124 when the pick 124 is in the pick receptacle 120.

Figure 5:
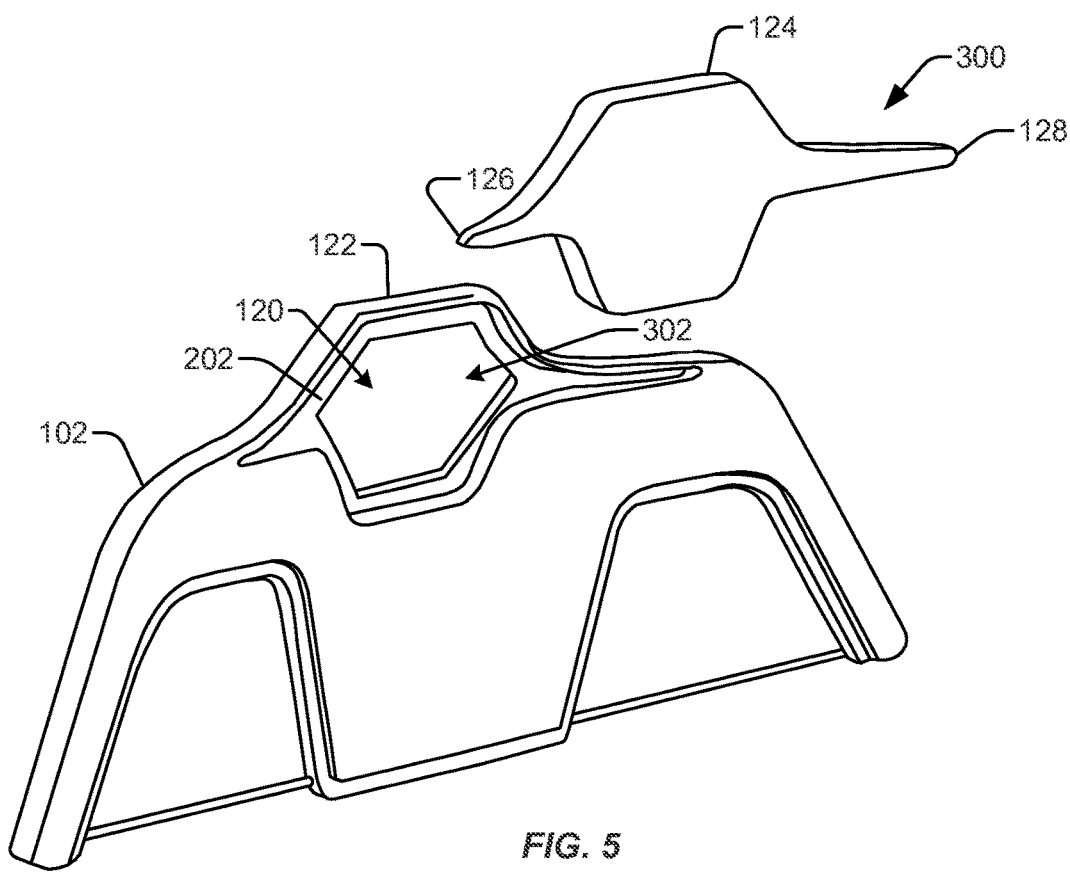
FIG. 5 is a perspective view of an embodiment of a hybrid dental tool that completely retains a pick within a pick receptacle.

With reference now to FIG. 5, a perspective view of an embodiment of a hybrid dental tool 300 is shown. This hybrid dental tool 300 includes the same features as the hybrid dental tool 100 with the exception of the pick receptacle 120. The hybrid dental tool 300 includes the flossing head 102 having a top 122 and a pick receptacle 120. The pick receptacle 120 shown in FIG. 5 is sized and shaped to receive the entire pick 124, and includes a back wall 202 that defines an access opening 302. In this embodiment, the pick 124 fits completely within the pick receptacle 120, and is removed from the pick receptacle 120 by the application of a force to the pick 124 through the access opening 302.

Figure 6:
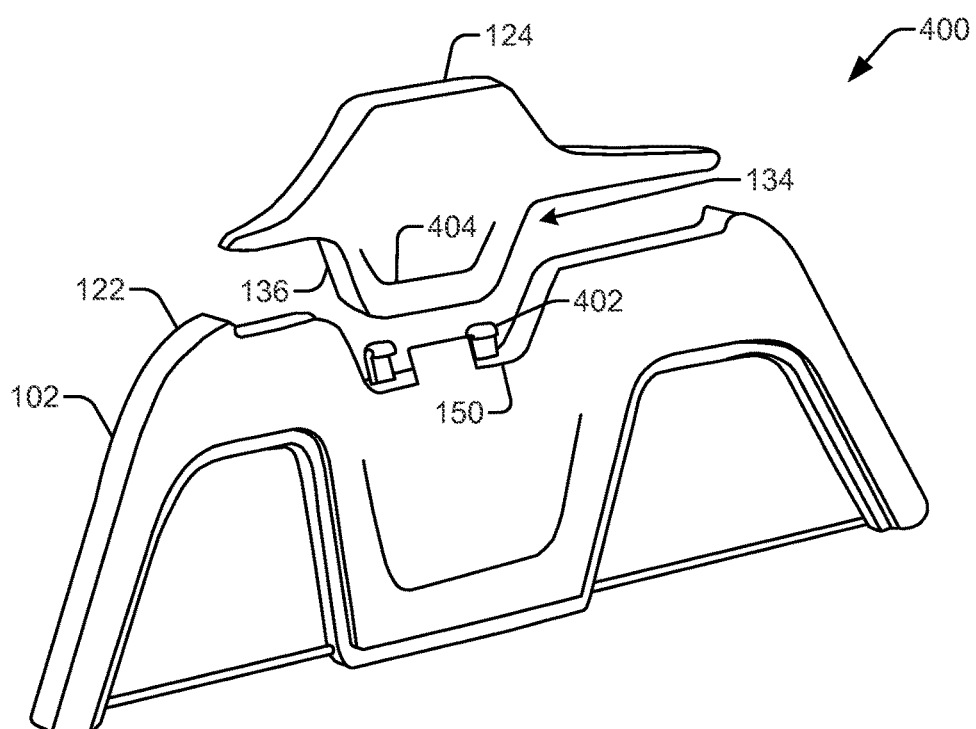
FIG. 6 is a perspective view of an embodiment of a hybrid dental tool that retains a pick with latches.

With reference now to FIG. 6, a perspective view of an embodiment of a hybrid dental tool 400 is shown. This hybrid dental tool 400 includes the same features as the hybrid dental tool 100 with the exception of the connection features 144 and the mating features 134. The hybrid dental tool 400 includes the flossing head 102 having a top 122 and a pick receptacle 120. The pick receptacle 120 shown in FIG. 6 includes a plurality of latches 402, which latches 402 can be, for example, compliant. In the embodiment of FIG. 6, the latches 402 are located on the bottom 150 of the pick receptacle 120, but in some embodiments, the latches 402 can be located on any features and/or component of the pick receptacle 120. The latches 402 of the flossing head 102 are configured to engage with the mating features 134 of the pick 124, and specifically to engage with a lip 404 located along all or portions of the insert 136.

Figure 7:
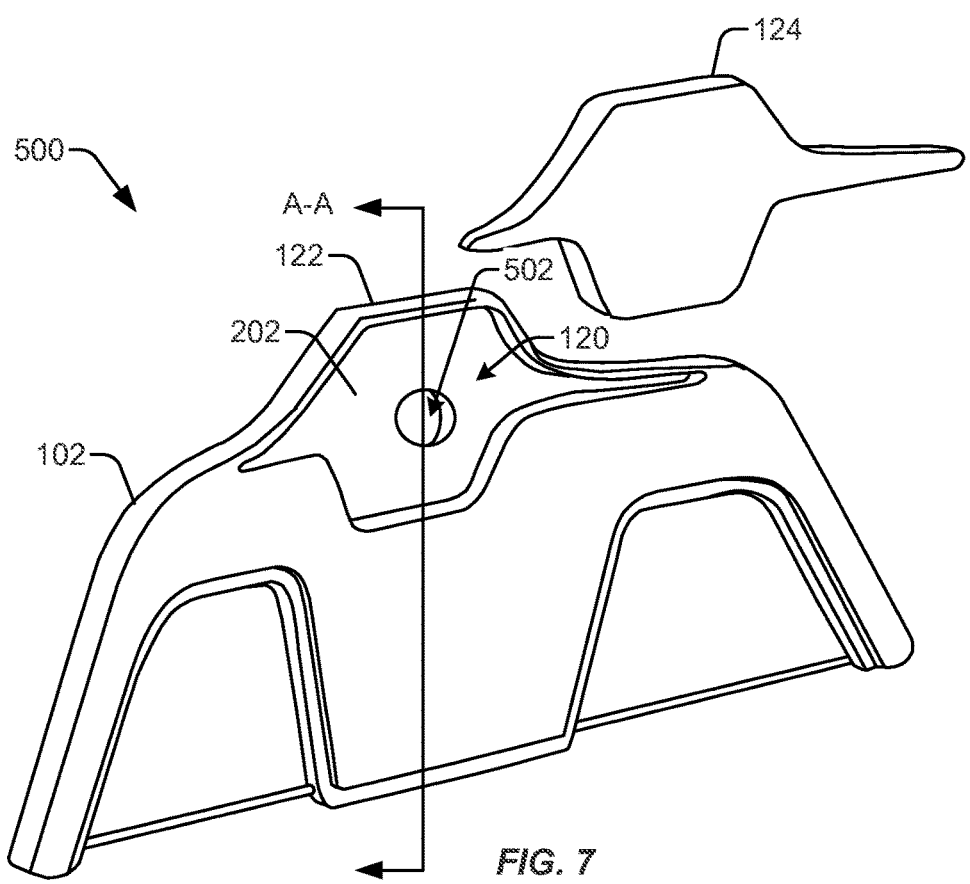
FIG. 7 is a perspective view of an embodiment of a hybrid dental tool that retains a pick with a securement insert.

With reference now to FIG. 7, a perspective view of an embodiment of a hybrid dental tool 500 is shown. This hybrid dental tool 500 includes the same features as the hybrid dental tool 100 with the exception of the connection features 144 and the mating features 134. The hybrid dental tool 500 includes the flossing head 102 having a top 122 and a pick receptacle 120. The pick receptacle 120 shown in FIG. 7 is sized and shaped to receive the entire pick 124, and includes a back wall 202 that defines an opening 502.

Figure 8:
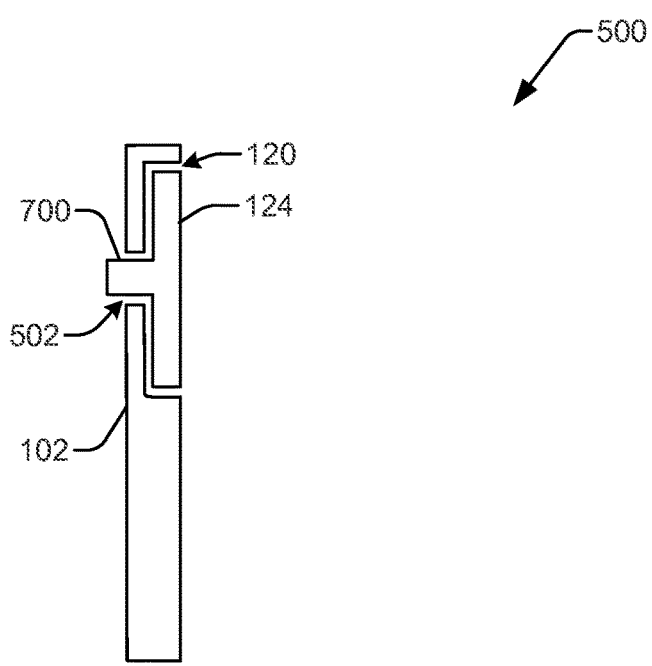
FIG. 8 is a section view of the embodiment of the hybrid dental tool of FIG. 7.

With reference now to FIG. 8, a section view of the hybrid dental device 500 is shown, which section is taken along plane A-A shown in FIG. 7. As seen in FIG. 8, the pick 124, which includes a securement insert 700, fits within the pick receptacle 120 and the securement insert 700 extends through opening 502 to thereby secure the pick within the pick receptacle 120 and to allow the separation of the pick 124 from the flossing head 102.

With reference now to FIG. 9, a perspective view of an embodiment of a hybrid dental tool 600 is shown. This hybrid dental tool 600 includes the flossing head 102 having a top 122 and a pick receptacle 120. The pick receptacle 120 shown in FIG. 7 is sized and shaped to receive the a portion pick 124, and includes a back wall 202 and front wall 900. The pick 124 shown in FIG. 9 includes the grip portion 132, the insert 136, and the abutment face 208 that is positioned on the pick 124 to abut top 122 of the flossing head 102 when the pick 124 is received within the pick receptacle 120.

With reference now to FIG. 10, a section view of the hybrid dental device 600 is shown, which section is taken along plane B-B shown in FIG. 9. As seen in FIG. 10, the pick 124, includes a step 902. Because of the step 902, the pick 124 fits within the pick receptacle 120 with the grip portion 132 adjacent to the back wall 202 and the insert 136 adjacent to the front wall 900. As further seen in FIG. 10, when the pick 124 is in the pick receptacle 120, the abutment surface 208 abuts the top 122 of the flossing head 102. This is further seen in FIG. 11.

Figure 12:
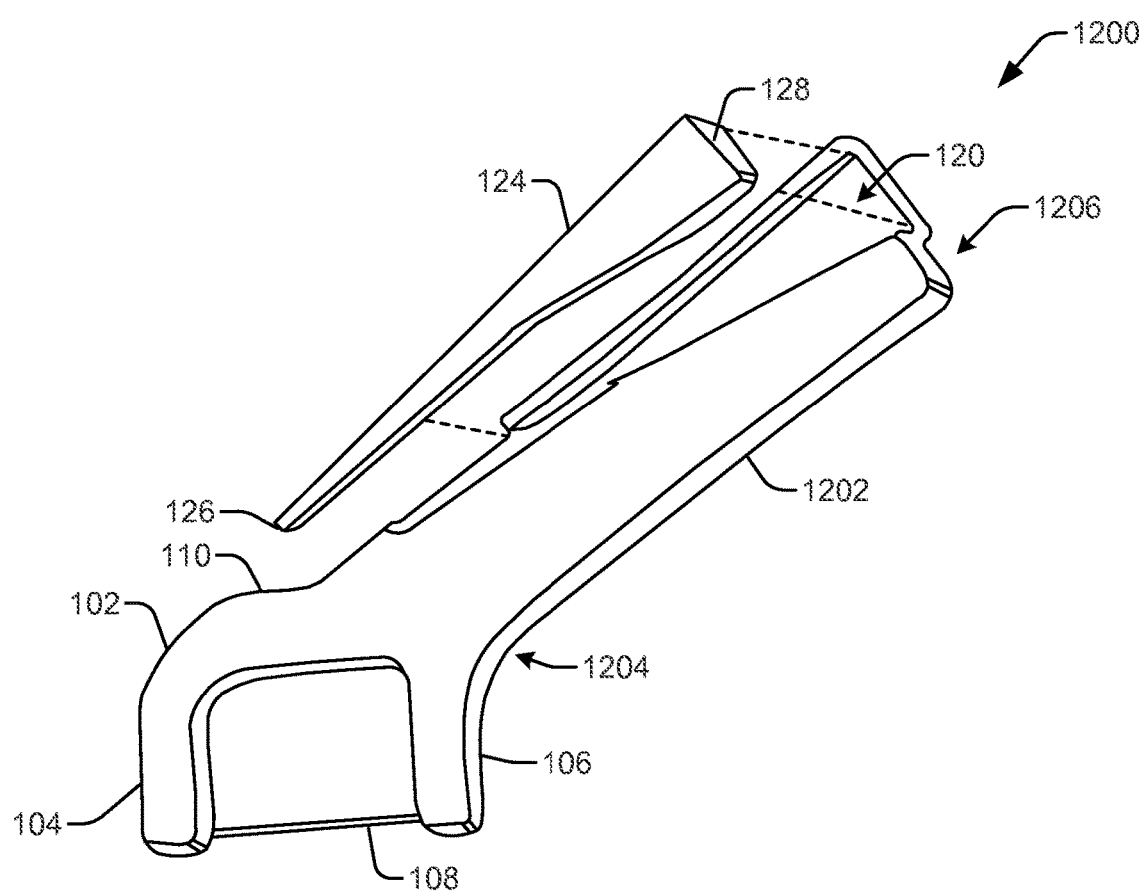
FIG. 12 is a perspective view of an embodiment of a hybrid dental tool with a handle including a pick receptacle.

With reference now to FIG. 12, a perspective view of an embodiment of a hybrid dental tool 1200 is shown. This hybrid dental tool 1200 includes the flossing head 102 having the first arm 104 and the second arm 106 connected by the first filament 108 and the link arm 110.

Extending from the flossing head is handle 1202. The handle 1202 can be sized and shaped so as to allow a user to hold the handle 1202 to control operation of the hybrid dental device 1200. In some embodiments, the handle 1202 can be made of the same material as the flossing head 102, and in some embodiments, the handle 1202 can be made of a different material than the flossing head 102. The handle 1202 can include a connecting end 1204 that connects to the flossing head 102, and specifically can connect to one or more of the link arm 110 and the second arm 106. The handle 1202 can further include a free end 1206. In some embodiments, the free end 1206 is located opposite the connecting end 1204, and does not directly connect to the flossing head 102, but rather connects to the flossing head 102 via the connecting end 1204.

The handle 1202 can include the pick receptacle 120. In the embodiment depicted in FIG. 12, the pick receptacle 120 extends from the free end 1206 of the handle 1202 towards the connecting end 1204 of the handle. The pick receptacle 120 can be shaped such that the first end 126 of the pick 124 is relatively more proximate to the connecting end 1204 of the handle 1202, and the second end 128 of the pick 124 is relatively more proximate to the free end 1206 of the handle 1202. In some embodiments, the pick receptacle 120 can be sized to be smaller than the pick 124 and/or so that one or several dimensions of the pick receptacle 120 are smaller than the corresponding one or several dimensions of the pick 124 to thereby create a friction fit and/or interference fit. In some embodiments, this interference fit can result in deformations to some or all of the pick receptacle 120 and/or the pick 124, which deformations can retain the pick 124 within the pick receptacle 120.

Figure 13:
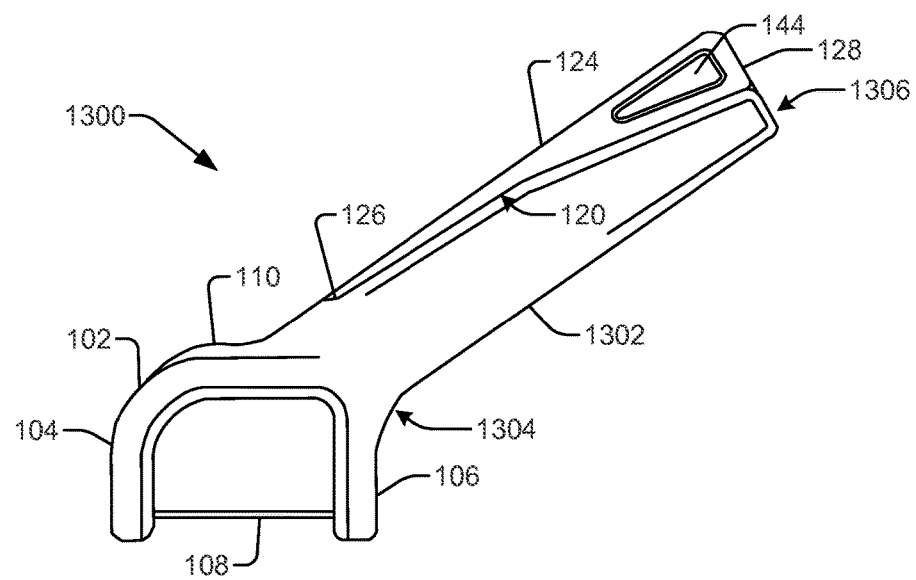
FIG. 13 is a front view of an embodiment of a hybrid dental tool with a handle including a pick receptacle.

With reference now to FIG. 13, a front view of an embodiment of a hybrid dental tool 1300 is shown. This hybrid dental tool 1300 includes the flossing head 102 having the first arm 104 and the second arm 106 connected by the first filament 108 and the link arm 110.

Extending from the flossing head is handle 1302. The handle 1302 can be sized and shaped so as to allow a user to hold the handle 1302 to control operation of the hybrid dental device 1300. In some embodiments, the handle 1302 can be made of the same material as the flossing head 102, and in some embodiments, the handle 1302 can be made of a different material than the flossing head 102. The handle 1302 can include a connecting end 1304 that connects to the flossing head 102, and specifically can connect to one or more of the link arm 110 and the second arm 106. The handle 1302 can further include a free end 1306. In some embodiments, the free end 1306 is located opposite the connecting end 1304, and does not directly connect to the flossing head 102, but rather connects to the flossing head 102 via the connecting end 1304.

The handle 1302 can include the pick receptacle 120 and the connecting features 144. In the embodiment depicted in FIG. 13, the pick receptacle 120 extends from the free end 1306 of the handle 1302 towards the connecting end 1304 of the handle. The pick receptacle 120 can be shaped such that the first end 126 of the pick 124 is relatively more proximate to the connecting end 1304 of the handle 1302, and the second end 128 of the pick 124 is relatively more proximate to the free end 1306 of the handle 1302.

Figure 14:
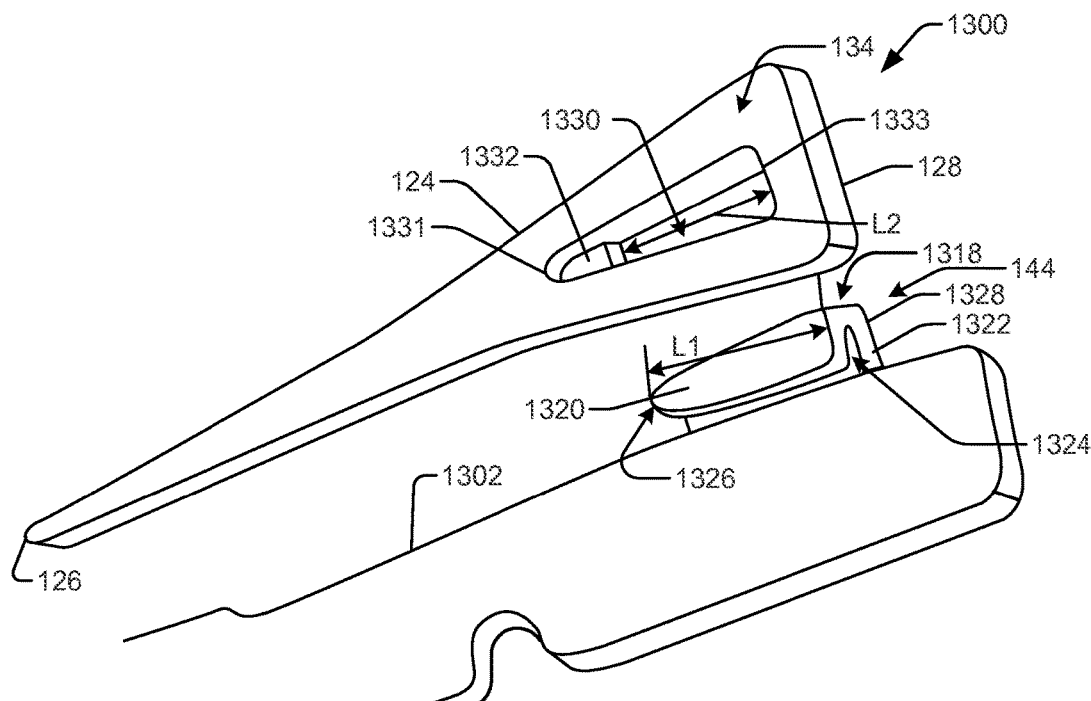
FIG. 14 is a close-up perspective view of the connecting features of the hybrid dental tool of FIG. 13.

With reference now to FIG. 14, a close-up perspective view of the connecting features 144 and the mating features 134 is shown. The connecting features 144 include a male insert 1318 having a front portion 1320 and a back portion 1322 that are partially separated by a void 1324. The male insert 1318 further includes a first end 1326 and an opposing second end 1328. The first end 1326 and the second end 1328 are separated by a distance L1.

The mating features 134 include a female receptacle 1330 that is sized and shaped to receive the male insert 1318. The female receptacle 1330 has a first end 1331 and a second end 1333. A retention tab 1332 is located at the first end 1331 of the female receptacle 1330. The retention tab 1332 is sized and shaped to be, at least partially, received within the void 1324 of the connecting features 144. As depicted in FIG. 14, the distance between the retention tab 1332 and the second end 1333 of the female receptacle 1330 is defined by a distance L2. In some embodiments, distance L2 can be greater than and/or equal to distance L1 to thereby allow the male insert 1318 to be received within the female receptacle 1330. In such an embodiment, after the male insert 1318 has been received in the female receptacle 1330, the male insert 1318, and the thereto connected pick 124, can be slid relatively towards the retention tab 1332 and/or the first end 1331 of the female receptacle 1330. This motion of the male insert 1318 with respect to the female receptacle 1330 can result in the retention tab 1332 being at least partially received within the void 1324 such that the front portion 1320 is on one side of the retention tab 1332 and the back portion 1322 is on the other, opposite side of the retention tab 1332. This positioning secures the male insert 1318, and thereby the pick 124, with respect to the flosser 101.

While various embodiments of present invention have been described, it will be apparent to those of skill in the art that many more embodiments and implementations are possible that are within the scope of this invention. Accordingly, the present invention is not to be limited to the described embodiments.

What is claimed is:

1. A hybrid dental device comprising:
   a pick having a grip portion located between a first pointed end a second pointed end, and a longitudinal axis extending between the first pointed end and the second pointed end; and
   a flosser comprising:
      a flossing head comprising:
         a first arm extending in a first direction;
         a second arm extending in the first direction; and
         a filament extending from the first arm to the second arm; and
      a pick receptacle configured to repeatedly capture the pick, wherein the pick receptacle is configured such that the first and second pointed ends of the pick are protected when the pick is received within the pick receptacle,
      wherein the grip portion of the pick extends away from and beyond the flosser when the pick is received within the pick receptacle.

2. The hybrid dental device of claim 1, wherein the pick receptacle is located on the flossing head.

3. The hybrid dental connector of claim 1, wherein the flossing head comprises a third arm extending from the flossing head and a second filament extending from the third arm to the second arm, wherein the third arm extends in the first direction from the flossing head.

4. The hybrid dental connector of claim 1, wherein the pick receptacle comprises a capture feature configured to releasably capture the pick.

5. The hybrid dental connector of claim 4, wherein the pick comprises a mating feature configured to mate with the capture feature of the flosser.

6. The hybrid dental device of claim 5, wherein the capture feature and the mating feature are configured to repeatedly capture the pick.

7. The hybrid dental device of claim 5, wherein the capture feature comprises at least one of:
   a pair of tabs;
   a receiving volume;
   a bracket; and
   an insert.

8. The hybrid dental device of claim 5, wherein the capture feature comprises:
   a bottom;
   a first wall extending in a second direction from the bottom;
   a second wall extending in a second direction from the bottom, wherein the bottom and the first and second walls define a receiving channel, wherein the receiving channel comprises a midline plane positioned between the first and second walls;
   a first tab extending from the first wall towards the midline plane; and
   a second tab extending from the second wall towards the midline plane.

9. The hybrid dental device of claim 8, wherein the first tab and the second tab are non-coplanar.

10. The hybrid dental device of claim 9, wherein the mating feature comprises a third tab configured to engage with both the first and second tabs.

11. The hybrid dental device of claim 1, wherein the pick and the flossing head comprise different materials.

12. The hybrid dental device of claim 11, wherein the flossing head comprises a polymer having a first material property and the pick comprises a polymer having a second material property, wherein the second material property is different than the first material property.

13. The hybrid dental device of claim 1, wherein both the first and second pointed ends of the pick are sized and shaped to allow insertion into the interproximal space between human teeth.

14. The hybrid dental device of claim 1, wherein the pick receptacle is located at the top of the flossing head.

15. A hybrid dental device comprising:
   a pick having a grip portion positioned between a first pointed end and a second pointed end and a longitudinal axis extending between said first pointed end and said second pointed end; and
   a flosser comprising:
      a flossing head comprising:
         a first arm extending in a first direction;
         a second arm extending in the first direction;
         a filament extending from the first arm to the second arm; and
         a pick receptacle located in the flossing head and configured to repeatedly capture the pick, wherein the pick receptacle is configured such that the first and second pointed ends of the pick are protected when the pick is received within the pick receptacle,
      wherein the grip portion of the pick extends away from and beyond the flossing head when the pick is received within the pick receptacle.

16. The hybrid dental connector of claim 15, wherein the pick receptacle comprises a capture feature configured to releasably capture the pick, and wherein the pick comprises a mating feature configured to mate with the capture feature of the flosser.

17. The hybrid dental device of claim 16, wherein the capture feature comprises:
   a bottom;
   a first wall extending in a second direction from the bottom;
   a second wall extending in a second direction from the bottom, wherein the bottom and the first and second walls define a receiving channel, wherein the receiving channel comprises a midline plane positioned between the first and second walls;
   a first tab extending from the first wall towards the midline plane; and
   a second tab extending from the second wall towards the midline plane.

18. The hybrid dental device of claim 17, wherein the first tab and the second tab are non-coplanar, wherein the mating feature comprises a third tab configured to deformably engage with both the first and second tabs.

19. The hybrid dental device of claim 15, wherein the pick receptacle is located at the top of the flossing head.

* * * * *